United States Patent [19]

Falling et al.

[11] 4,454,340

[45] Jun. 12, 1984

[54] PREPARATION OF ARYL 1-HYDROXYARYL-2-CARBOXYLATES

[75] Inventors: Stephen N. Falling; Alan K. Wilson, both of Kingsport, Tenn.

[73] Assignee: Eastman Kodak Company, Rochester, N.Y.

[21] Appl. No.: 499,607

[22] Filed: May 31, 1983

[51] Int. Cl.³ .................................... C07C 69/76
[52] U.S. Cl. ................................ 560/56; 560/72
[58] Field of Search ...................... 560/56, 72, 71

[56] References Cited

U.S. PATENT DOCUMENTS

| | | | |
|---|---|---|---|
| 1,858,627 | 5/1932 | Korten et al. | 560/56 |
| 1,947,819 | 2/1937 | Zitscher et al. | 562/467 |
| 3,036,116 | 5/1962 | Muxfeldt et al. | 560/56 |
| 3,248,422 | 4/1966 | Elslager et al. | 560/56 |
| 3,803,245 | 4/1974 | Lodewijk | 562/467 |
| 4,340,498 | 7/1982 | Sugimori | 560/56 |

*Primary Examiner*—Paul J. Killos
*Attorney, Agent, or Firm*—J. Frederick Thomsen; Daniel B. Reece, III

[57] ABSTRACT

Disclosed is a process for the preparation of aryl 1-hydroxyaryl-2-carboxylates by the reaction of certain phenolic compounds with an aryl chloroformate in the presence of aluminum chloride and an organic solvent.

3 Claims, No Drawings

PREPARATION OF ARYL 1-HYDROXYARYL-2-CARBOXYLATES

DESCRIPTION

This invention concerns the preparation of certain aryl 1-hydroxyaryl-2-carboxylates by the reaction of certain phenolic compounds with an aryl chloroformate in the presence of aluminum chloride and an organic solvent.

One embodiment of our invention pertains to the preparation of aryl 1-hydroxy-2-naphthoates which are intermediates used in large volumes in the chemical industry and are particularly important in the manufacture of photographic chemicals. Such compounds may be prepared by carboxylating 1-naphthol and converting the 1-hydroxy-2-naphthoic acid obtained to its aryl ester.

We have discovered that aryl 1-hydroxy-2-naphthoates can be prepared directly from 1-naphthols by reacting a 1-naphthol with an aryl chloroformate in the presence of aluminum chloride and an organic solvent. Our novel process is unique in that all or essentially all, depending on the reaction conditions employed, of the acylation of 1-naphthols occurs at the ortho position.

Although the preparation of aryl benzoates, aryl toluates and aryl chlorobenzoates by the reaction of an aryl chloroformate with the appropriate aromatic compound is known [J. Org. Chem., 22, 325 (1957); J. Appl. Poly. Sci., 9, 3295 (1965)], the acylation of phenolic compounds with aryl chloroformates is believed to be novel. German Offenlegungsschrift No. 3,108,076 discloses a process for the preparation of mixtures of ortho and para acylphenols by the reaction of an acyl halide such as acetyl chloride with phenol in the presence of aluminum chloride and a halobenzene. We have found that the reaction of acetyl chloride with 1-naphthol in refluxing dichloromethane in the presence of aluminum chloride gives 60.8% o-acetyl-1-naphthol, 23.8% p-acetyl-1-naphthol and 11.2% 1-naphthyl acetate.

The process of this invention can be utilized to prepare aryl 1-hydroxy-2-naphthoates (or aryl 1-hydroxy-2-naphthalenecarboxylates) wherein the aryl group and the remainder of the naphthalene ring are unsubstituted or substituted with groups of atoms which groups are inert to the reactants under the reaction conditions and which do not inhibit or otherwise affect the intended course of the reactions. The process is illustrated schematically by:

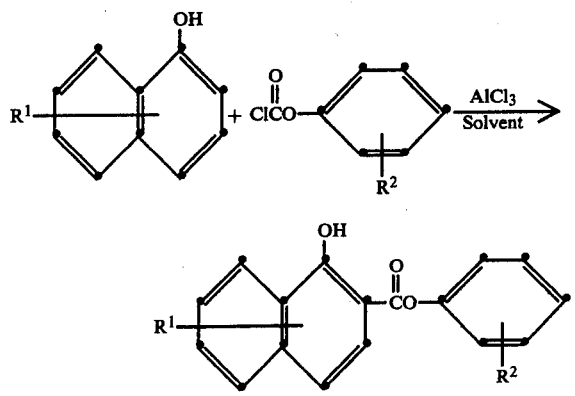

wherein $R^1$ and $R^2$ independently are selected from hydrogen, alkyl or alkoxy of up to about six carbon atoms or halogen and may be present at any ring position except the position ortho to the naphthol hydroxy group.

The process may be carried out at typical acylation temperatures such as temperatures in the range of about 30° to 200° C. although the use of temperatures near the bottom of the given range will require prolonged reaction times and those at the opposite end of the range will require the use of solvents which, because of their boiling points, are not easily separated from the aryl 1-hydroxy-2-naphthoate product. Thus, the reaction preferably is performed at a temperature in the range of about 80° to 120° C. Suitable organic solvents are those which have the appropriate boiling points and in which the aluminum chloride/product complex is partially or totally soluble. Examples of such solvents include aliphatic and aromatic chlorohydrocarbons such as dichloromethane, 1,2-dichloroethane, 1,2-dichloropropane, tetrachloroethylene, chlorobenzene and o-dichlorobenzene and aromatic hydrocarbons such as benzene, toluene and xylene. Because of a number of considerations, including toxicity, waste disposal and boiling point, toluene is the preferred solvent. Although toluene, like other aromatic hydrocarbons, is not inert, the 1-naphthol reactant reacts faster than toluene and the crystalline aryl 1-hydroxy-2-naphthoate product is easily separated from the liquid toluene-derived co-products.

In the practice of the process, aluminum chloride is added to a mixture of the 1-naphthol reactant and solvent followed by the addition of the aryl chloroformate. Best results are obtained when the molar ratio of aluminum chloride:1-naphthol reactant is about one and the molar ratio of aryl chloroformate:1-hydroxy-2-naphthoate product can be recovered by decomposing the aluminum chloride/product complex formed initially by adding water or an aqueous mineral acid to the reaction mixture, removing the aqueous phase and concentrating the organic phase after washing the latter one or more times with water, dilute mineral acid and/or dilute base.

A second embodiment of our invention comprises the preparation of aryl 4-alkoxy-2-hydroxybenzoates by the reaction of a 3-alkoxyphenol with an aryl chloroformate in the presence of aluminum chloride and an organic solvent according to the procedure described hereinabove. The reaction of 3-alkoxyphenols with an aryl chloroformate is unique in that other phenols, including phenol itself, either do not react, give low yields of the desired benzoate ester and/or result in the formation of the corresponding aryl carbonates. The aryl 4-alkoxy-2-hydroxybenzoates are useful chemical intermediates, for example, in the preparation of the stabilizers disclosed in U.S. Pat. No. 3,896,125.

Our novel process is further illustrated by the following examples.

EXAMPLE 1

To a 500-mL, three-neck, nitrogen-purged flask were added 28.8 g (0.20 mole) of 1-naphthol and 90 mL of toluene. To this stirred slurry was added 26.6 g (0.20 mole) of anhydrous aluminum chloride in portions over five minutes. The temperature of the mixture rose to 40°–50° C. during this addition. The orange slurry was heated to reflux, then 32.0 g (0.204 mole) of phenyl chloroformate was added over a period of 30 minutes. After this addition, the mixture was refluxed for 30 minutes then cooled to 30°–40° C. To the red reaction mixture was added 100 mL of water while holding the temperature at 35°–50° C. This addition is very exothermic initially, and ice bath cooling is used. During addition of the remaining water, the bath is lowered or removed in order to avoid cooling below 35° C. After this addition, 20 mL of 32% hydrochloric acid was added quickly at 35°–50° C. The mixture was stirred for 15 minutes, then the layers are allowed to separate. The lower (aqueous) layer was discarded. The top layer was washed (at 40°–50° C.) successively with: two 100-mL portions of 10% hydrochloric acid and two 100-mL portions of 40°–50° C. water. The solvent was then stripped off under vacuum (150-200 mm) to a pot temperature of 90° C. To the resulting amber liquid was added 120 mL of isopropyl alcohol at 70° C. The solution was cooled slowly to 0°–5° C. After stirring at 0°–5° C. for one hour, the slurry was filtered and the solids washed with three 25-mL portions of 0°–5° C. isopropyl alcohol. The yellow solids were air dried at 40° C. to give 31.5 g (59.7%) of phenyl 1-hydroxy-2-naphthoate.

EXAMPLE 2

Example 1 was repeated using 4-methyl-1-naphthol. The yield of phenyl 1-hydroxy-4-methyl-2-naphthoate (light tan, m.p. 76°–77° C.) obtained was 45%.

EXAMPLE 3

To a 500-mL, three-neck, nitrogen-purged flask was added 17.9 g (0.10 mole) of 4-chloro-1-naphthol, 100 mL of methylene chloride, 15 g (0.11 mole) of anhydrous aluminum chloride, and 15 mL (0.12 mole) of phenyl chloroformate. This mixture was heated to reflux. After 48 hours, the mixture was cooled to 10° C. and 200 mL of water and 15 mL of 37% hydrochloric acid were added. To this mixture was added 100 mL of ethyl acetate. The layers were separated and the organic layer was washed with two 100-mL portions of 5N hydrochloric acid. The organic layer was dried with anhydrous magnesium sulfate, filtered, then the solvent stripped off under vacuum. The resulting oil solidified and the crude product was recrystallized from isopropyl alcohol. The yield of phenyl 4-chloro-1-hydroxy-2-naphthoate (off-white, m.p. 102°–104° C.) obtained was 54%.

EXAMPLE 4

To a 1,000-mL, three-neck, nitrogen-purged flask was added 26.5 g (0.21 mole) of 3-methoxyphenol, 215 mL of methylene chloride, 32 g (0.24 mole) of aluminum chloride and 32 mL (0.26 mole) of phenyl chloroformate. This mixture was heated to reflux. After 24 hours, the mixture was cooled to 20°–30° C. and 400 mL of water and 32 mL of 37% hydrochloric acid were added. The layers were separated and the organic layer washed with two 100-mL portions of 5N hydrochloric acid. The organic layer was dried with anhydrous magnesium sulfate, filtered, then the solvent stripped off under vacuum. The crude product was recrystallized from heptane. The yield of phenyl 2-hydroxy-4-methoxybenzoate (white, m.p. 61.5°–62.5° C.) obtained was 49%.

This invention has been described in detail with particular reference to preferred embodiments thereof, but it will be understood that variations and modifications can be effected within the spirit and scope of the invention.

We claim:

1. Process for the preparation of aryl 1-hydroxy-2-naphthoates which comprises reacting a 1-naphthol with an aryl chloroformate in the presence of aluminum chloride and an organic solvent.

2. Process for the preparation of phenyl 1-hydroxy-2-naphthoate which comprises reacting at a temperature of about 80° to 120° C. 1-naphthol and phenyl chloroformate in the presence of aluminum chloride and toluene.

3. Process for the preparation of aryl 4-alkoxy-2-hydroxybenzoates which comprises reacting 3-alkoxyphenol with an aryl chloroformate in the presence of aluminum chloride and an organic solvent.

* * * * *